(12) United States Patent
Lau et al.

(10) Patent No.: US 6,954,730 B2
(45) Date of Patent: Oct. 11, 2005

(54) SYSTEM AND METHOD FOR ASSISTING DIAGNOSIS AND TREATMENT OF TEMPOROMANDIBULAR JOINT CONDITIONS

(75) Inventors: Kenneth U. Lau, Pendleton, IN (US); Nelson Mark, Middletown, IN (US)

(73) Assignee: JKL Software Development LLC, Pendleton, IN (US)

( * ) Notice: Subject to any disclaimer, the term of this patent is extended or adjusted under 35 U.S.C. 154(b) by 33 days.

(21) Appl. No.: 10/440,993

(22) Filed: May 19, 2003

(65) Prior Publication Data

US 2004/0006432 A1 Jan. 8, 2004

Related U.S. Application Data

(63) Continuation-in-part of application No. 10/172,921, filed on Jun. 17, 2002, now abandoned.
(60) Provisional application No. 60/381,929, filed on May 20, 2002, and provisional application No. 60/299,121, filed on Jun. 18, 2001.

(51) Int. Cl.$^7$ .......................... G01N 33/48; G06F 7/00; G06G 7/48
(52) U.S. Cl. .............................. 705/2; 705/3; 702/19; 706/48; 706/924; 707/6
(58) Field of Search .......................... 705/2, 3; 702/19; 706/48, 924; 707/6

(56) References Cited

U.S. PATENT DOCUMENTS

| | | | |
|---|---|---|---|
| 4,836,218 A | 6/1989 | Gay et al. | |
| 4,858,121 A | 8/1989 | Barber et al. | |
| 5,225,976 A | 7/1993 | Tawil | |
| 5,255,187 A | 10/1993 | Sorensen | |
| 5,301,105 A | 4/1994 | Cummings, Jr. | |
| 5,437,278 A | 8/1995 | Wilk | |
| 5,463,548 A | 10/1995 | Asada et al. | |
| 5,519,607 A | 5/1996 | Tawil | |
| 5,644,778 A | 7/1997 | Burks et al. | |
| 5,772,585 A | 6/1998 | Lavin et al. | |
| 5,878,746 A | 3/1999 | Lemelson et al. | |
| 5,890,129 A | 3/1999 | Spurgeon | |
| 6,047,259 A * | 4/2000 | Campbell et al. | 705/3 |
| 6,063,026 A | 5/2000 | Schauss et al. | |
| 6,088,677 A | 7/2000 | Spurgeon | |
| 6,090,044 A | 7/2000 | Bishop et al. | |
| 6,484,144 B2 * | 11/2002 | Martin et al. | 705/2 |

OTHER PUBLICATIONS

Yap, A. U. J. et al. Journal of Oral Rehabilitation (Jan. 2001) vol. 28 pp. 78–87.*

Douglas H Morgan, D.D.S., The Great Imposter—Diseases of the Temporomandibular Joint, Journal of the American Medical Association, May 31, 1976, vol. 235, No. 22, p. 2395.

Wesley E. Shankland, II, D.D.S., M.S., Ph.D., Migraine and Tension–Type Headache Reduction Through Pericranial Muscular Suppression: A Preliminary Report, The Journal of Craniomandibular Practice, 2001, p. 269, Chroma, Inc.

Applegren, Anna; Appelgren, Björn; Kopp, Sigvard; Lundeberg, Thomas; Theodorsson, Elvar; "Neuropeptides in the Arthritic TMJ and Symptoms and Signs from the Stomatognathic System with Special Consideration to Rheumatoid Arthritis," Journal of Orofacial Pain, Summer 1995, pp. 215–224, vol. 9, No. 3.

Bergamini, M.; Galletti, S. Prayer; Bergamini, C.; "An Updated on Myofascial Pain Syndrome and Related Muscle–Skeletal Disorders Affecting the Masticatory Apparatus," photocopy, 7, no date.

Bjorne, A.; Agerberg, G.; "Craniomandibular Disorders in Patients with Meniere's Disease: A Controlled Study," Journal of Orofacial Pain, Winter 1996, pp. 28–36, vol. 10, No. 1.

Bouquot, Jerry E.; McMahon, Robert E.; Ischemic Osteonecrosis in Facial Pain Syndromes: Part 1: A Review of Nico (Neuralgia–Inducing Cavitational Osteonecrosis) Based on Experience with More Than 2,000 Patients, Sep. 1996, p. 1, Edition 5.

Brunelle, J. A.; Bhat, M.; Lipton, J. A.; "Prevalence and Distribution of Selected Occlusal Characteristics in the US Population, 1988–1991," Journal of Dental Research, Feb. 1996, pp. 706–713, vol. 75 (Special Issue).

Carlson, Charles R.; Bertrand, Peter M.; Ehrlich, A. Dale; Maxwell, Austin W.; Burton, Richard G.; "Physical Self–Regulation Training for the Management of Temporomandibular Disorders," Journal of Orofacial Pain, 2001, pp. 47–55, vol. 15, No. 1.

Chuong, Robert; Piper, Mark A.; Boland, Thomas J.; "Osteonecrosis of the Mandibular Condyle," Oral Surgery Oral Medicine Oral Pathology, May 1995, pp. 539–545.

Dao, Thuan T. T.; LaVigne, Gilles J.; Charbonneau, Anne; Feine, Jocelyne S.; Lund, James P.; "The Efficacy of Oral Splints in the Treatment of Myofascial Pain of the Jaw Muscles: a Controlled Clinical Trial," Pain, 1994, pp. 85–94, vol. 56.

Dawson, Peter E., Evaluation, Diagnosis, and Treatment of Occlusal Problems, 2nd ed., 1989, pp. 85–89, 113, 500–503, 524, 555; C.V. Mosby Company, St Louis.

(Continued)

Primary Examiner—Mary K. Zeman
(74) Attorney, Agent, or Firm—Barnes & Thornburg LLP

(57) ABSTRACT

A method and system for assisting diagnosis and treatment of temporomandibular joint disease. The steps of the method include recording physical symptoms; conducting a plurality of medical examinations related to temporomandibular joint disease; creating a diagnostic criteria based on conditions known to be a factor in diagnosis of temporomandibular joint disease; and determining which of a plurality of patients match the diagnostic criteria.

10 Claims, 10 Drawing Sheets

OTHER PUBLICATIONS

Falace, Donald A.; Reid, Keven; Rayens, Mary Kay; "The Influence of Deep (Odontogenic) Pain Intensity, Quality, and Duration on the Incidence and Characteristics of Referred Orofacial Pain," Journal of Orofacial Pain, 1996, pp. 232–239, vol. 10, No. 3.

Goldberg, Michael B.; Mock, David; Ichise, Masanori; Proulx, Guy; Gordon, Allan; Shandling, Maureen; Tsai, Scott; Tenebaum, Howard C.; "Neuropsychologic Deficits and Clincal Features of Posttraumatic Temporomandibular Disorders," Journal of Orofacial Pain, Spring 1996, pp. 126–140, vol. 10, No. 2.

Heir, G. M.; Fein, L.A.; "Lyme Disease: Considerations for Dentistry," Journal of Orofacial Pain, Winter 1996, pp. 74–86, vol. 10, No. 1.

Kamelchuk, Lorne S.; Major, Paul W.; "Degenerative Disease of the Temporomandibular Joint," Journal of Orofacial Pain, 1996, pp. 168–180, vol. 9, No. 2.

Kaplan, Andrew S.; Assael, Leon A.; Temporomandibular Disorders, Diagnosis and Treatment, 1991, pp. 106–107, 119–125, 134, 579, W. B. Saunders Company, Philadelphia.

Kimmel, Saul, "Temporomandibular Disorders and Occlusion: An Appliance to Treat Occlusion Generated Symptoms of TMD in Patients Presenting with Deficient Anterior Guidance," The Journal of Craniomandibular Practice, Oct. 1994, pp. 234–240, vol. 12, No. 4.

Kolbinson, Dean A.; Epstein, Joel B.; Burgess, Jeffrey A.; "Temporomandibular disorders, Headaches, and Neck Pain Following Motor Vehicles Accidents and the Effect of Litigation: Review of the Literature," Journal of Orofacial Pain, Spring 1996, pp. 101–124, Vol. 10, No. 2.

Kopp, Sigvard, "Neuroendocrine, Immune, and Local Responses Related to Temporomandibular Disorders," Journal of Orofacial Pain, 2001, pp. 9–28, vol. 15, No. 1.

Kuboki, Takuo; Azuma, Yoshiharu; Orsini, Maria G.; Takenami, Yasushi; Yamashita, Atsushi; "Effects of Sustained Unilateral Molar Clenching on the Temporomandibular Joint Space," Oral Surgery Oral Medicine Oral Pathology, Dec. 1996, pp. 616–624, vol. 82, No. 6.

Kuhn, Walter F.; Kuhn, Sharon C.; Gilberstadt, Hudson; "Occipital Neuralgias: Clinical Recognition of a Complicated Headache. A Case Series and Literature Review," Journal of Orofacial Pain, 1997, pp. 158–165, vol. 11, No. 2.

Laskin, Daniel M., "The Clinical Diagnosis of Temporomandibular Disorders in the Orthodontic Patient," Senminars in Orthodontics, Dec. 1995, pp. 197–206, vol. 1, No. 4.

Lauret, Jean Francios; Le Gall, Marcel G.; "The Function of Mastication: A Key Determinant of Dental Occlusion," Practical Periodontics & Aesthetic Dentistry, Nov./Dec. 1996, pp. 807–818, vol. 8, No. 8.

Marcel, Tom, et al., "Magnetic Resonance Spectroscopy of the Human Masseter Muscle in Nonbruxing and Bruxing Subjects," Journal of Orofacial Pain, 1995, pp. 116–130, vol. 9, No. 2.

Marguelles–Bonnet, Richard E.; Carpentier, P.; Yung, J. P.; Defrennes, D.; Pharaboz, C.; "Clinical Diagnosis Compared with Findings of Magnetic Resonance Imaging in 242 Patients with Internal Derangement of the TMJ," Journal of Orofacial Pain, 1995, pp. 244–253, vol. 9, No. 3.

Marien, Jr., Manuel, "Trismus: Causes, Differential Diagnosis, and Treatment," General Dentistry, Jul.–Aug. 1997, pp. 350–355.

McNamara, Jr., James A.; Seligman, Donald A.; Okeson, Jeffrey P.; "Occlusion, Orthodontic Treatment, and Temporomandibular Disorders: A Review," Journal of Orofacial Pain, 1995, pp. 76–78, vol. 9, No. 1.

McNeill, Charles, "History and Evolution of TMD Concepts," Oral Surgery Oral Medicine Oral Pathology, Jan. 1997, pp. 51–60, vol. 83, No. 1.

Miles, Dale A., et al.; Oral and Maxillofacial Radiology, 1991, pp. 23–25, 52, 128–130; W. B. Saunders Company, Philadelphia.

Mongini, Franco; Ciccone, Giovannino; Ibertis, Francesca; Negro, Cesare; "Personality Characteristics and Accompanying Symptoms in Temporomandibular Joint Dysfunction, Headache, and Facial Pain," Journal of Orofacial Pain, 2000, pp. 52–58, vol. 14, No. 1.

Morgan, Douglas H., "Tinnitus of TMJ Origin: a Preliminary Report," The Journal of Craniomandibular Practice, Apr. 1992, pp. 124–129, vol. 10, No. 2.

Morrow, David; Tallents, Ross H.; Katzberg, Richard W.; Murphy, William C.; Hart, Thomas C.; "Relationship of Other Joint Problems and Anterior Disc Position in Symptomatic TMD Patients and in Asymptomatic Volunteers," Journal of Orofacial Pain, 1996, pp. 15–19, vol. 10, No. 1.

Okeson, Jeffrey P.; Management of Temporomandibular Disorders and Occlusion, 1993, pp. 124, 219, 190, Mosby–Year Book, Inc., St. Louis.

Okeson, Jeffrey P.; Management of Temporomandibular Disorders and Occlusion, 4th Edition, 1998, pp. 342, 445, 461, 463, Mosby–Year Book, Inc., St. Louis.

Rakai, Robert E., Conn's Current Therapy 1996, 1996, pp. 948–950, W. B. Saunders Company, Philadelphia.

Rakal, Robert E., Conn's Current Therapy 1997, 1997, pp. 1006–1011, W. B. Saunders Company, Philadelphia.

Rakal, Robert E., Conn's Current Therapy 1998, 1998, pp. 986–990, W. B. Saunders Company, Philadelphia.

Rakal, Robert E., Conn's Current Therapy 1999, 1999, pp. 234–236, 921–922, 947–948, 997–1004, W. B. Saunders Company, Philadelphia.

Sanders, Bruce, "Management of Internal Derangements of the Temporomandibular Joint," Seminars in Orthodontics, Dec. 1995, pp. 244–257, vol. 1, Nov. 4.

Seligman, Donald A.; Pullinger, Andrew G.; "The Role of Functional Occlusal Relationships in Temporomandibular Disorders; A Review," Journal of Craniomandibular Disorders: Facial & Oral Pain, 1991, pp. 265–279, vol. 5, No. 4.

Silbert, Robert K., "Fibromyalgia and Temporomandibular Disorders," Jan. 15, 1996, photocopy, 1.

Suvinen, Tuija i.; Reade, Peter C.; "Temporomandibular Disorders: A Critical Review of the Nature of Pain, and Its Assessment," Journal of Orofacial Pain 1995, pp. 317–339, vol. 9, No. 4.

Tanne, Kazuo; Tanaka, Eiji; Sakuda, Mamoru; "Stress Distributions in the TMJ During Clenching in Patients with Vertical Discrepancies of the Craniofacial Complex," Journal of Orofacial Pain, 1995, pp. 153–160, vol. 9, No. 2.

Tominaga K.; Fujiki, T.; Mizuno, A.; Sato, H.; Izumi, M.; Uetani, M.; "Synovial Chondromatosis of the Temporomandibular Joint," Dentomaxillofacial Radiology, Feb. 1995, pp. 59–62, vol. 24.

Travell, Janet G.; Simons, David G.; Myofascial Pain and Dysfunction: The Trigger Point Manual, 1983, pp. 276–277, Williams & Wilkins, Baltimore.

Wabeke, Kya B.; Hansson, Tore L.; Hoogstraten, Johan; Van Der Kuy, Piet; "Temporomandibular Joint Clicking: A Literature Overview," Journal of Craniomandibular Disorders: Facial & Oral Pain, 1989, pp. 163–173, vol. 3, No. 3.

Wilkes, Clyde H., "Internal Derangements of the Temporomandibular Joint," Archives of Otolaryngology–Head & Neck Surgery, Apr. 1989, pp. 469–477, vol. 115.

Wright, Edward. F.; Gullickson, Dale C.; "Dental Pulpalgia Contributing to Bilateral Preauricular Pain and Tinnitus," Journal of Orofacial Pain, 1996, p. 166, vol. 10, No. 2.

* cited by examiner

SYSTEM AND METHOD FOR ASSISTING DIAGNOSIS AND TREATMENT OF TEMPOROMANDIBULAR JOINT CONDITIONS

RELATED APPLICATION

The present application is a Continuation-in-Part of U.S. patent application, Ser. No. 10/172,921, filed on Jun. 17, 2002, now abandoned, entitled "System and Method for Assisting Diagnosis and Treatment of Temporomandibular Joint Conditions," which is related to and claims priority to U.S. Provisional Patent Application, Ser. No. 60/299,121, filed on Jun. 18, 2001, entitled "Method and System for Diagnosis and Treatment of Temporomandibular Joint Conditions." The present application is also related to and claims priority to U.S. Provisional Patent Application, Ser. No. 60/381,929, filed on May 20, 2002, entitled "Orthosis Thickness and Its Effects on TM Joint Space." To the extent not included below, the subject matter disclosed in those applications is hereby expressly incorporated into the present application.

BACKGROUND OF THE INVENTION

The present invention is related to conditions of the jaw, and more specifically to a system and method for diagnosis and treatment of temporomandibular joint conditions.

Temporomandibular joint disease (TMJ) is a term that is generally associated with diseases and/or conditions within the teeth, jaw bone, and related musculature which result in a variety of symptoms. These symptoms range from mild to severe, and include headaches, facial pain, as well as pain and cracking in the jaw. More severe symptoms may include seizures, memory loss, abnormal thyroid activity, rashes, sleep disturbances, and nausea. For a given case, any one of these symptoms may be experienced either alone or as a combination of symptoms. Moreover, these symptoms may be indicative of conditions other than TMJ. Consequently, proper diagnosis of TMJ is difficult.

The diagnosis of TMJ is further complicated by the fact that there is a lack of scientific inquiry into the etiologic or underlying cause of TMJ. Etiologic causes, which may occur alone or in combination, are thought to include trauma, disease, genetics, oral habits, dental work, surgical procedures, malocclusion (e.g., over-bite and cross-bite), and stress. The lack of understanding as to the etiologic cause has contributed to the divergence in opinion within various professions as to how to treat TMJ. The lack of scientific inquiry into the causes of TMJ necessarily results in a dearth of scientific inquiry into the effectiveness of various treatment protocols.

For the individual suffering from the disruptive symptoms of TMJ, obtaining proper diagnosis and treatment is frequently not the end of the problems related to TMJ. Because of the nescient state of diagnosis and treatment of TMJ, many insurance programs are unwilling to cover the potentially extensive expenses required to diagnose and treat the disorder. Consequently, the individual may not have the independent financial wherewithal necessary for obtaining proper diagnosis and treatment.

It is desired to assist in the diagnosis and treatment of TMJ by providing a method and system for doing the same. Furthermore, it is desired to reduce the role and time of individuals in determining the potential for insurance coverage and for submitting the documentation required by various insurance programs.

An illustrative embodiment disclosed herein provides a method for assisting diagnosis and treatment of temporomandibular joint disease. The steps of the method comprise recording physical symptoms experienced by a plurality of patients; conducting a plurality of medical examinations related to temporomandibular joint disease on each of the plurality of patients; creating a diagnostic criteria based on conditions known to be factors in diagnosis of temporomandibular joint disease; wherein the conditions are selected from the physical symptoms experienced by the plurality of patients and the results of the plurality of medical examinations of each of the plurality of patients; and determining which of the plurality of patients match the diagnostic criteria.

In other illustrative embodiments, the diagnostic criteria may be selected from at least one of a group comprising locations of pain, symptoms, medical examinations, and mitigating and aggravating circumstances; the medical examinations being selected from at least one of a group comprising a dental exam, an x-ray exam, a biometric exam and a muscle exam; the match of the diagnostic criteria being a complete match or a partial match; and the step of selecting treatment protocols for patients that completely match the diagnostic criteria and for patients that partially match the diagnostic criteria.

Another illustrative embodiment disclosed herein also provides a method of assisting in diagnosing a condition of a patient. This embodiment comprises the steps of providing a database configured to receive and sort data; conducting an examination of the patient; wherein the examination comprises a plurality of medical tests related to the condition; inputting results of the examination into the database; inputting symptoms of the condition being experienced by the patient into the database; and matching the results of the examination and the symptoms of the condition in the database with a diagnosis of the condition for determining a treatment protocol.

Other illustrative embodiments may comprise one or more steps of: inputting a treatment protocol and results of said treatment protocol; inputting successful treatment protocols of the condition; inputting patient and insurance information for payment and treatment authorization; inputting case histories from a plurality patients; and inputting symptoms from a plurality of patients.

Another illustrative embodiment disclosed herein also provides a system for assisting diagnosis and treatment of temporomandibular joint disease. The system comprises a computerized database, a symptoms module, a medical examinations module, and a diagnostic module. The computerized database is configured to receive modules containing data. The symptoms module records and stores a plurality of symptom data experienced by a plurality of patients. The medical examinations module comprises data from a plurality of medical examinations related to temporomandibular joint disease on each of the plurality of patients. The diagnostic module is in communication with the symptoms and medical examinations modules such that the diagnostic module comprises a plurality of diagnostic criteria based on conditions known to be a factor in diagnosis of temporomandibular joint disease. An operator can then create a selected diagnostic criteria to establish a basis for diagnosis of temporomandibular joint disease. The diagnostic module searches the plurality of symptom data and the data from the plurality of medical examinations to find which of the plurality of patients match the selected diagnostic criteria.

Other illustrative embodiments may comprise the diagnostic criteria being selected from at least one of a group comprising locations of pain, symptoms, medical examinations, and mitigating and aggravating circumstances; the medical examinations being selected from at least one of a group comprising a dental exam, an x-ray exam, a biometric exam and a muscle exam; and the match of the selected diagnostic criteria being a complete match or a partial match.

Additional features and illustrative embodiments of the disclosure will become apparent to those skilled in the art upon consideration of the following detailed description exemplifying the best mode of carrying out the embodiments as presently perceived.

BRIEF DESCRIPTION OF DRAWINGS

The present disclosure will be described hereafter with reference to the attached drawings which are given as non-limiting examples only, in which.

Corresponding reference characters indicate corresponding parts throughout the several views. The exemplification set out herein illustrates embodiments of the system and method, and such exemplification is not to be construed as limiting the scope of the system and method in any manner.

DETAILED DESCRIPTION OF THE DRAWINGS

Figure 1:
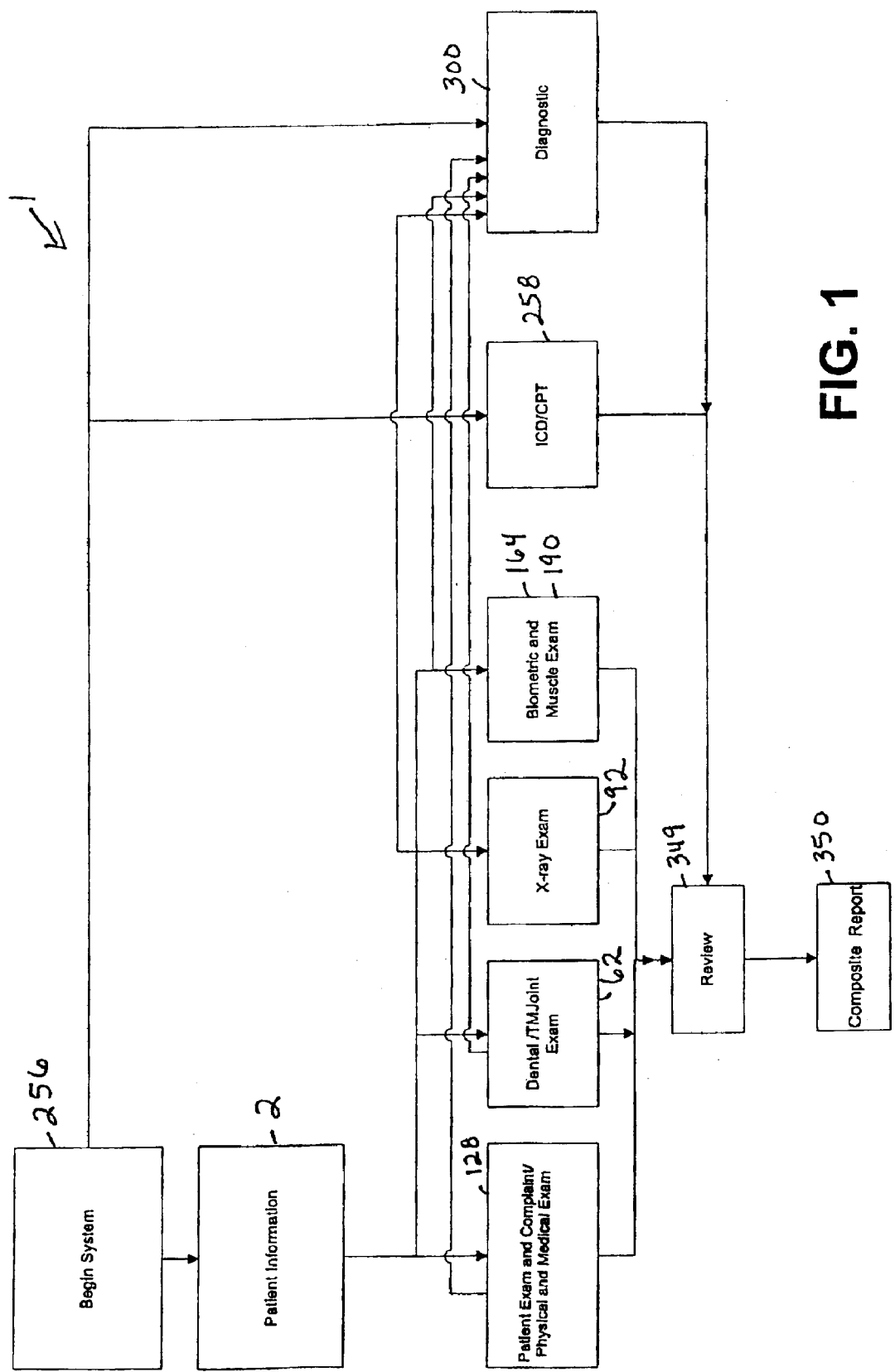
FIG. 1 is a diagrammatic flow chart of a system for assisting the diagnosis of a condition such as TMJ.

An illustrative embodiment of the disclosure is shown in FIG. 1, which depicts a diagrammatic flow chart of a system for assisting the diagnosis of TMJ 1. System 1 begins at system start 256 to initiate the program. The illustrated system is a computer program that can be used in a hospital, physician's office, or clinic. System 1 comprises several modules that receive data and coordinate with each other to assist in the diagnosis and treatment of a condition like TMJ. In the illustrated embodiment, the patient information module 2, the patient complaint and exam module 28, the dental exam module 62, the x-ray exam module 92, the biometric and muscle exam modules 164, 190, respectively, and the International Classification of Disease/Current Procedural Terminology (ICD/CPT) module 258 coordinate with the Diagnostic condition criteria module 300. A physician, such as a dentist or orthodontist, for example, may then search for a condition or a selected group of conditions that were recorded in at least one of the modules 2, 28, 62, 92, 164 or 190 to find which patients may have TMJ. The diagnostic module 300 of system 1 finds all patients with either all or some of the conditions selected by the physician. The physician may then evaluate what treatment protocols are available and appropriate for the patents as suggested by the ICD/CPT module 258, or may develop a custom treatment protocol, or even a hybrid protocol drawing from the ICD/CPT treatment and the custom treatment protocols. The results of the modules can be reviewed at 349 and a composite reports module 350 allows the dentist or orthodontist to compile and print reports from each module 2, 28, 62, 92, 164, 190 either individually or collectively. These reports can be used for insurance purposes or as status letters for referring doctors.

Figure 2:
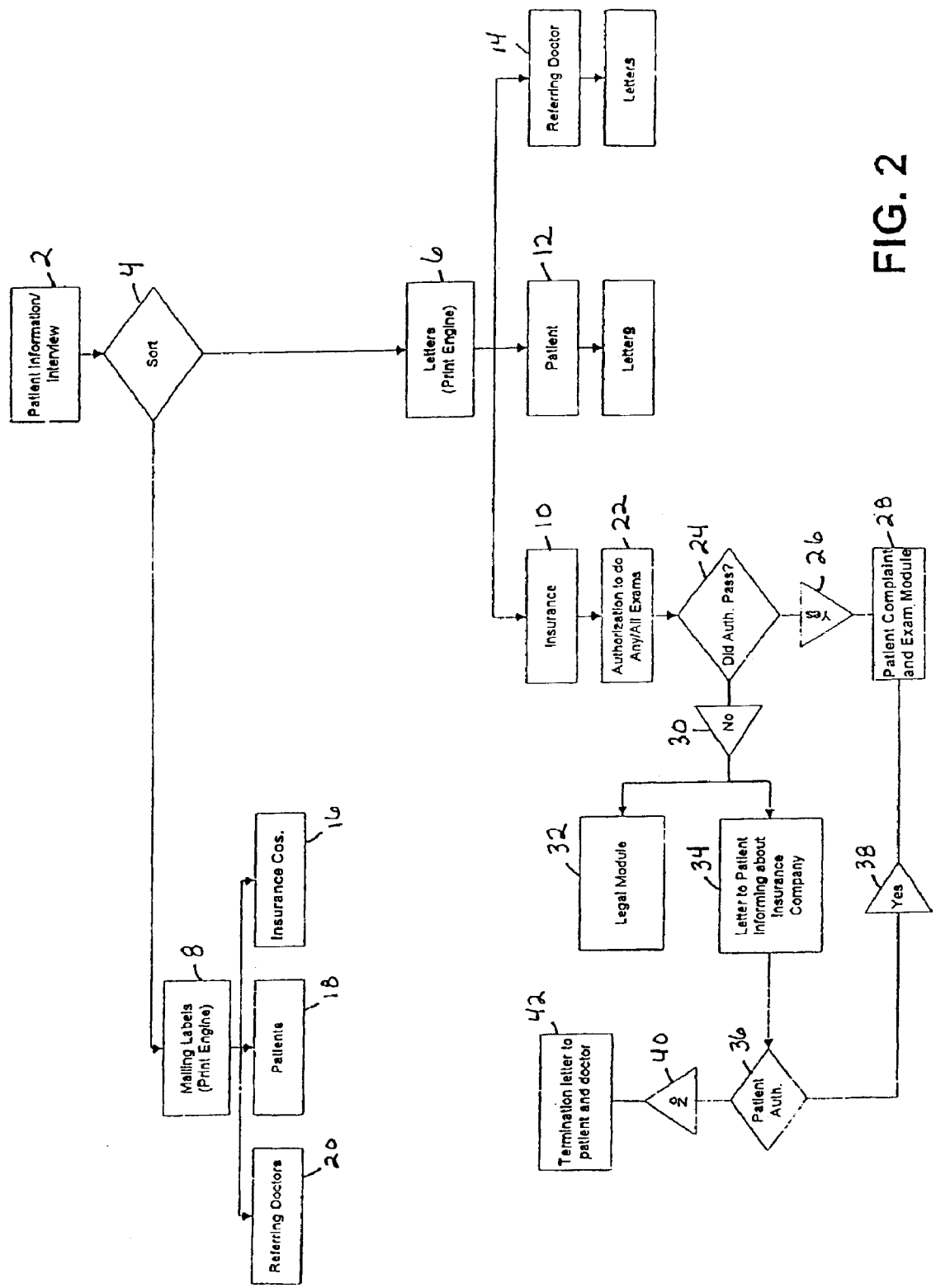
FIG. 2 is a diagrammatic flow chart of a patient information module.

Referring now to FIG. 2, the illustrative system comprises of patient information module 2. This module 2 is where all the personal information about a patient is entered and stored. For example, address, date of birth, social security number, gender, and marital status information will all be entered in patient information module 2 for use in conjunction with other modules. Additionally, insurance information can be recorded and stored in this module as well. The patient information module 2 may, thus, comprise a complete profile of the patient in which that information can then be sorted at 4 so that the appropriate letters at 6 and mailing labels at 8 can be generated. The illustrative system contemplates generating insurance claim requests at 10, patient information letters at 12, and referring doctor status letters at 14. The mailing label engine will also print corresponding mailing labels at 16, 18, and 20, respectively.

Specifically regarding the insurance sub module 10, all necessary information that the insurance company typically needs to process a claim will be included in a request for authorization to conduct examination at 22. The decision by the insurance company will determine what the patient information module 2 will do next. The decision making process is represented by reference number 24. If the insurance company authorizes the examination at 26, the system will proceed to the patient complaint and exam module 28, further discussed herein. If the insurance company denies authorization, however, the patient information module 2 will either be directed towards the legal module at 32, or a letter will be generated informing the patient of the insurance company's decision at 34. If the patient provides a secondary means for examination authorization at 36 and 38, then the patient information module 2 will proceed to the patient complaint and exam module 28. If no such secondary authorization is provided at 40, then a termination letter to the patient and the referring doctor will be issued at 42.

Figure 3:
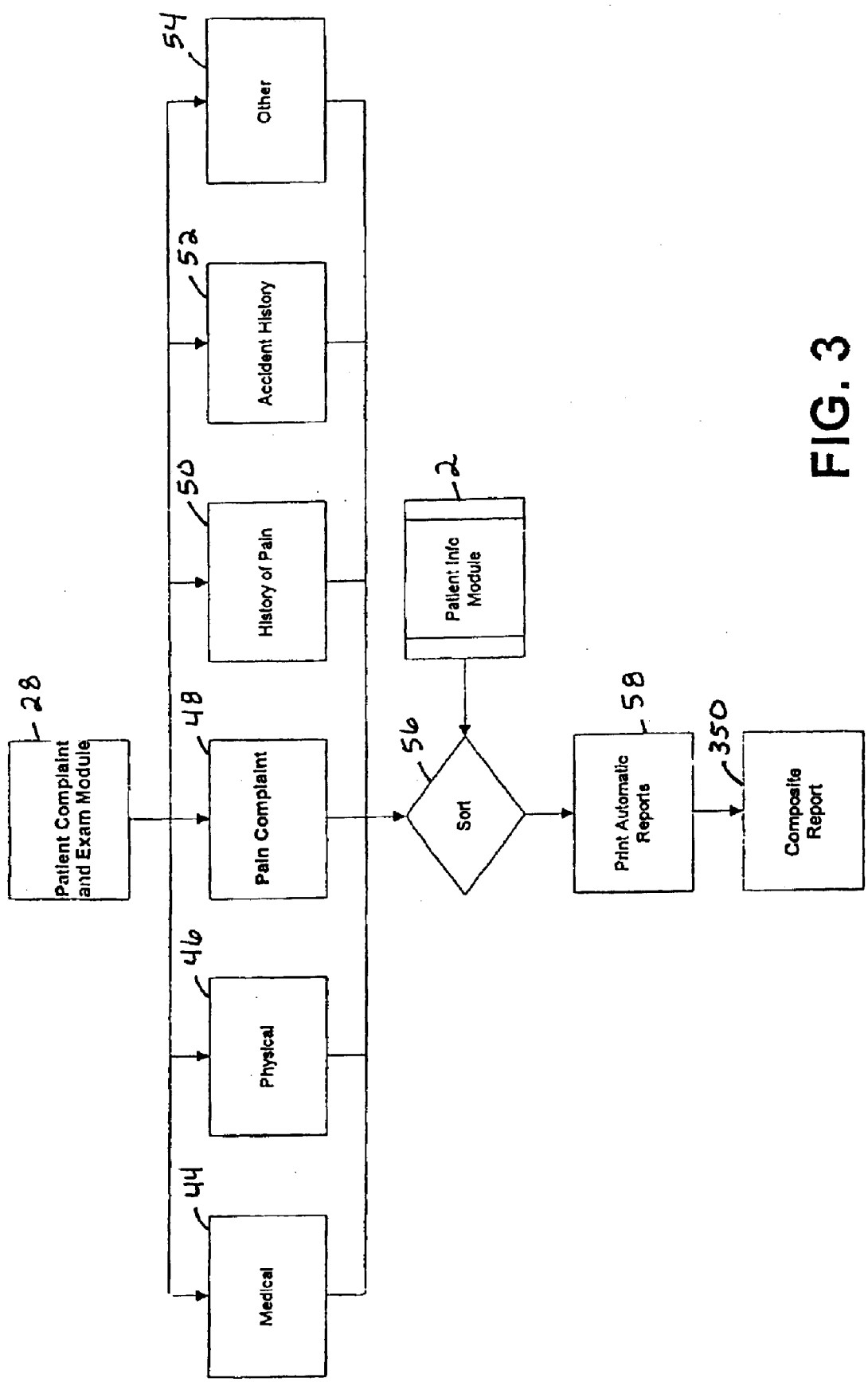
FIG. 3 is a diagrammatic flow chart of a patient exam and complaint module.

Once insurance authorization has been completed, the system continues to the patient complaint and exam module 28, as shown in FIG. 3. This module records and stores all the medical information about the patient. For example, medical information at 44 may include a survey of food or drug allergies, any possible blood diseases, arthritides degenerative disease, neurological disease, endocrine/gynecological issues, previous medical diagnostic tests, gastro-intestinal/respiratory issues, circulatory issues, habits, smoking/non-smoking, family medical history, current medication taken, if any, etc. Also, a physical assessment of the patient can be conducted at 46. This may include general posture of the patient, and in the case of TMJ, facial asymmetry, head posture, eye structure, chin structure, extremity tremors, nose structure, equilibrium, cranial nerve screening, cranial nerve evaluation, and vital signs (i.e., blood pressure, pulse rate).

The patient complaint section 48 is where the patient provides information regarding the specific symptoms they are experiencing related to the believed TMJ pain. For example, section 48 is where the patient is to describe the specific areas and types of pain, and the duration and intensity of the pain in those particular locations. It is contemplated that such descriptions can be given either rhetorically through description, or graphically through a model, for example, where the patient can pinpoint those areas on the model where he or she is experiencing pain, and for what duration and in what intensity. This provides the patient complaint and exam module 28 with a detailed recitation of the type of pain and the location of the pain the patient is experiencing. In addition, if there are believed known causes of the pain, such as an accident, information surrounding these circumstances can be recorded and stored by the patient complaint and exam module 28 at the history of pain section 50. This section illustratively includes a detailed account of the accident, including what had occurred, and how such pain had resulted from the accident. The accident history section 52 records and stores specific accident history detail, such as time, date, location, nature of injuries sustained during the accident, etc. Lastly, after all the medical physical complaint pain history and accident history information have been recorded and stored, if there is additional information that may be relevant but was not appropriate for either of those sections, the other section at 54 is available to enter such miscellaneous information.

Once all of the information from sections 44 through 54 are collected, they are sorted at 56 with the information or data from patient information module 2 so that reports can be generated at 58, and reviewed by the patient and amended, if necessary. A patient complaint report is produced at 58 which is used as a portion of the composite report 350.

Figure 4:
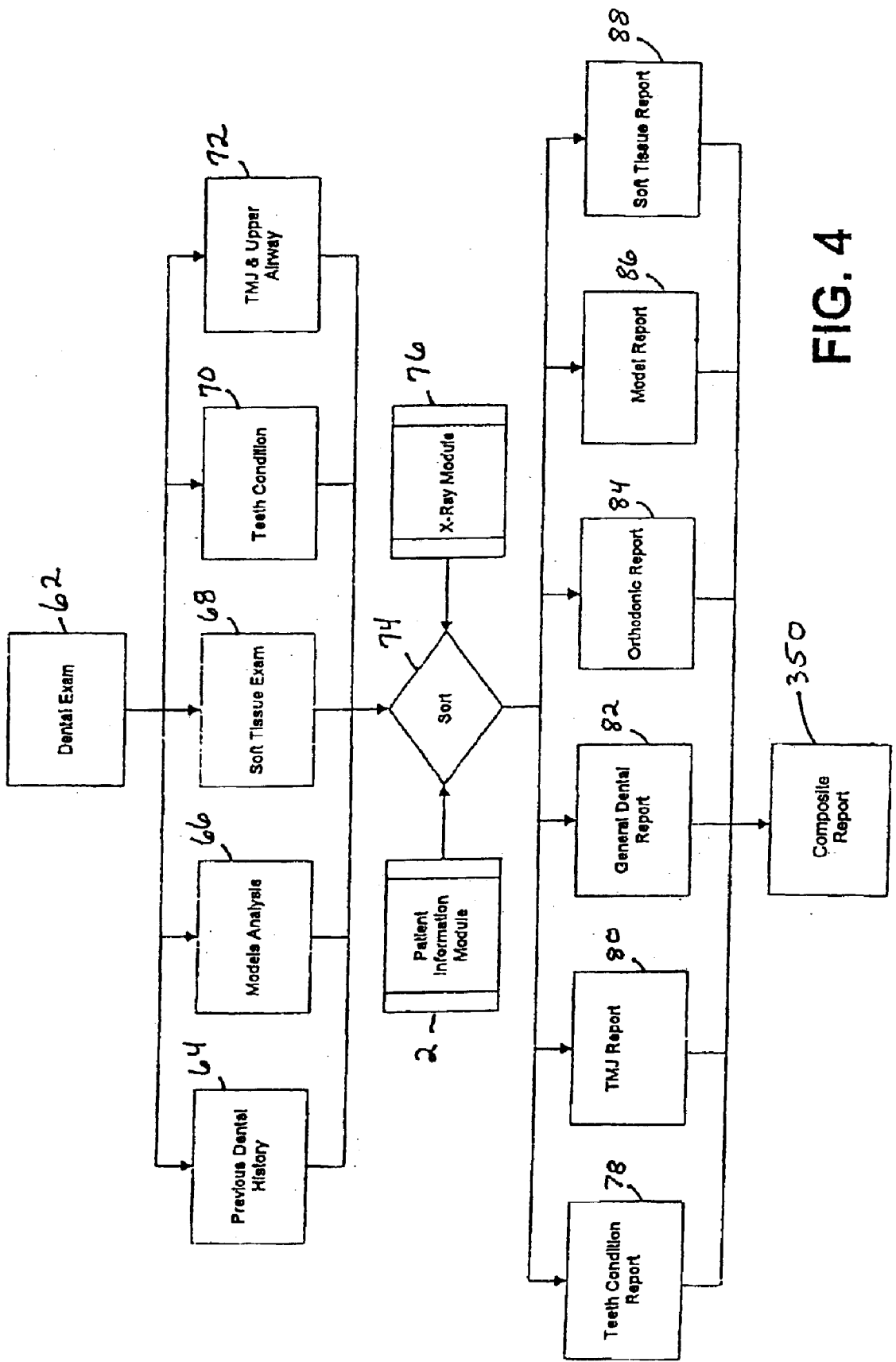
FIG. 4 is a diagrammatic flow chart of a dental examination module.

After all of the patient's personal and complaint information or data is entered into the system, a dental exam 62 can be conducted as shown in FIG. 4. This dental exam module 62 first comprises a section for previous dental history at 64, which comprises recordation and storage of all the patient's known previous dental history, including previous treatments made to the teeth, gums, or mouth, as well as storage of any other pertinent dental history. A model analysis can be recorded and stored in section 66 as well. This includes collection of data from the patient's occlusal diagnostic model. Specifically, data of horizontal and vertical relationships can be recorded along with the overall shape of the maxilla and mandible. Furthermore, the occlusal wear facets can be accurately recorded. It is contemplated that in this section, a digitized image of the patient's diagnostic model can be imported for visual inspection by the physician. A soft tissue examination at 68 can also be recorded and stored. This section allows the physician to collect a soft tissue profile of the head and neck of the patient. Illustratively, the soft tissue exam includes the facial profile, shape of the tongue, throat, and the general health of supporting tissue of the teeth. Additionally the physician can record the condition of the patient's teeth at 70 as well as record the condition of the jaw further TMJ symptoms and upper airway of the patient at 72.

All of this information is merged with the patient information module 2 and sorted at 74. In addition, information from the x-ray module 76, as will be discussed further herein, will be merged to produce a series of reports 78 through 88. Each report will provide a particular aspect of the patient's condition. For example, the teeth condition report 78 will contain data from the teeth condition section 70, the TMJ report will contain data regarding the patient's TMJ symptoms, the general dental report will contain data from the previous dental history section 64, the orthodontic report will draw data from all sections 64 through 72, the model report 86 will contain data from the model analysis 66, and the soft tissue report 88 will contain data from the soft tissue exam 68. These reports can then be integrated into the composite report 350.

Figure 5:
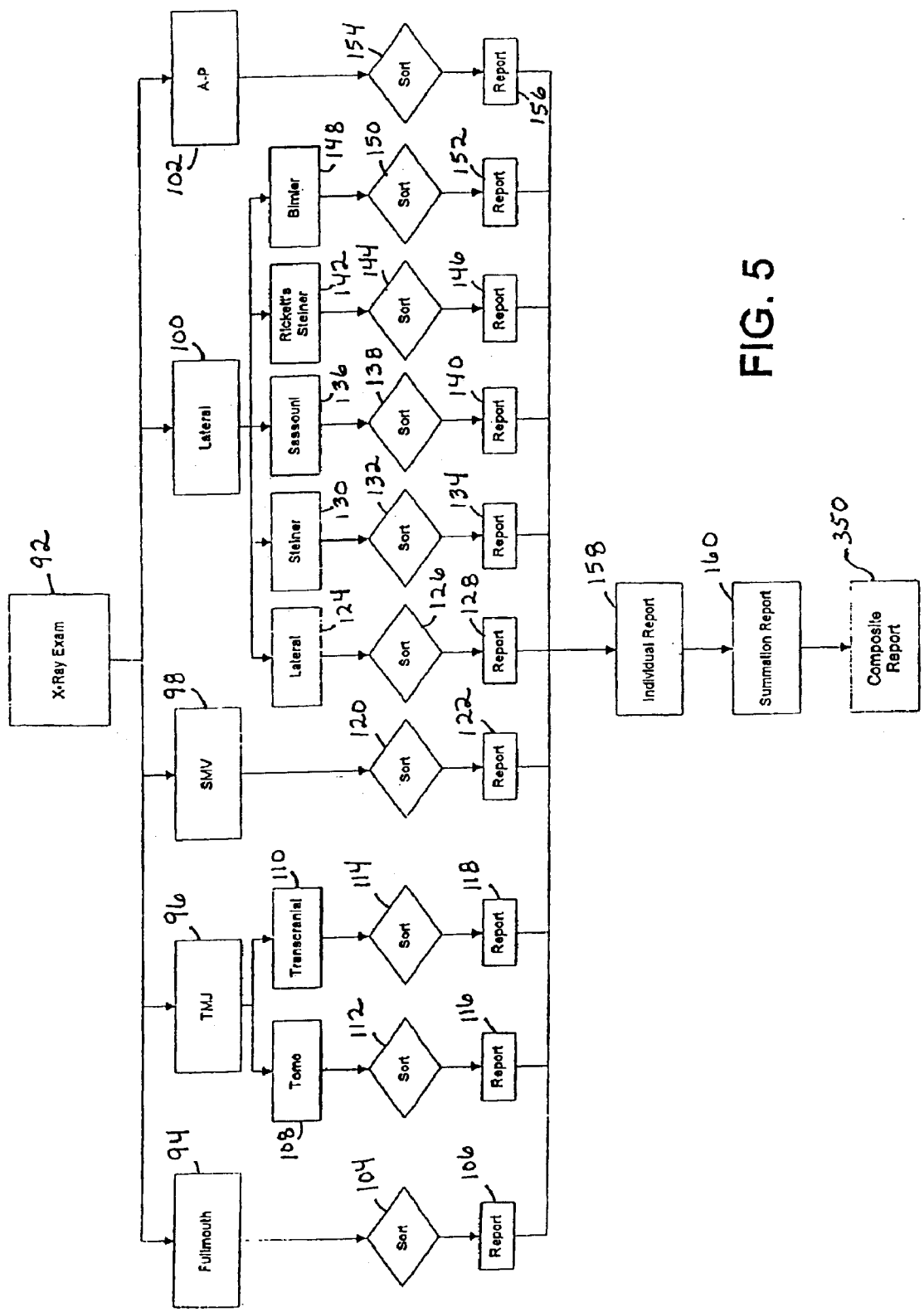
FIG. 5 is a diagrammatic flow chart of an x-ray examination module.

To provide the physician with information regarding the internal skeletal anatomical relationship of the head and neck, and the maxilla to the mandible, an x-ray module 92, as shown in FIG. 5, records and stores a battery of x-ray exams. Such x-ray exams include the full mouth at 94, the tomography of the temporomandibular joint at 96, the submental vortex view at 98, the lateral head plate view at 100, and the anterior-posterior head plate view at 102. Regarding the full mouth exam at 94, once that exam has been taken, the resulting x-ray information will be sorted at 104, and a report generated at 106. Regarding the TMJ x-ray exam at 96, again the tomography of the TMJ will be measured at 108, as well as the transcranial measurement at 110, the results of which are each sorted at 112 and 114, respectively, with resulting reports generated at 116 and 118, respectively. With regard to the submental vortex view at 98, again, the resulting exam information will be sorted at 120, and a report generated at 122. With regard to the lateral head plate view at 100, a lateral measurement will be taken at 124. That information or data will be sorted at 126, and a report generated at 128. In addition, a Steiner cephalometric measurement will be taken at 130, the data of which will be sorted at 132, and a report generated at 134. In addition, a Sassouni cephalometric measurement will be taken at 136, the data of which is sorted at 138, and resulting report generated at 140. A Rickett's Steiner cephalometric measurement 142 will also be taken, the data of which will be sorted at 144, and a report generated at 146. Finally, a Bimler cephalometric measurement will be taken at 148, the data of which will be sorted at 150, and resulting report generated at 152. The data from the anterior-posterior head plate view at 102 will, too, be sorted at 154, and a report generated at 156. Subsequently, an individual report with results from all of these exams is generated at 158, as well as a summation report at 160 which contributes to the composite report 350.

Figure 6:
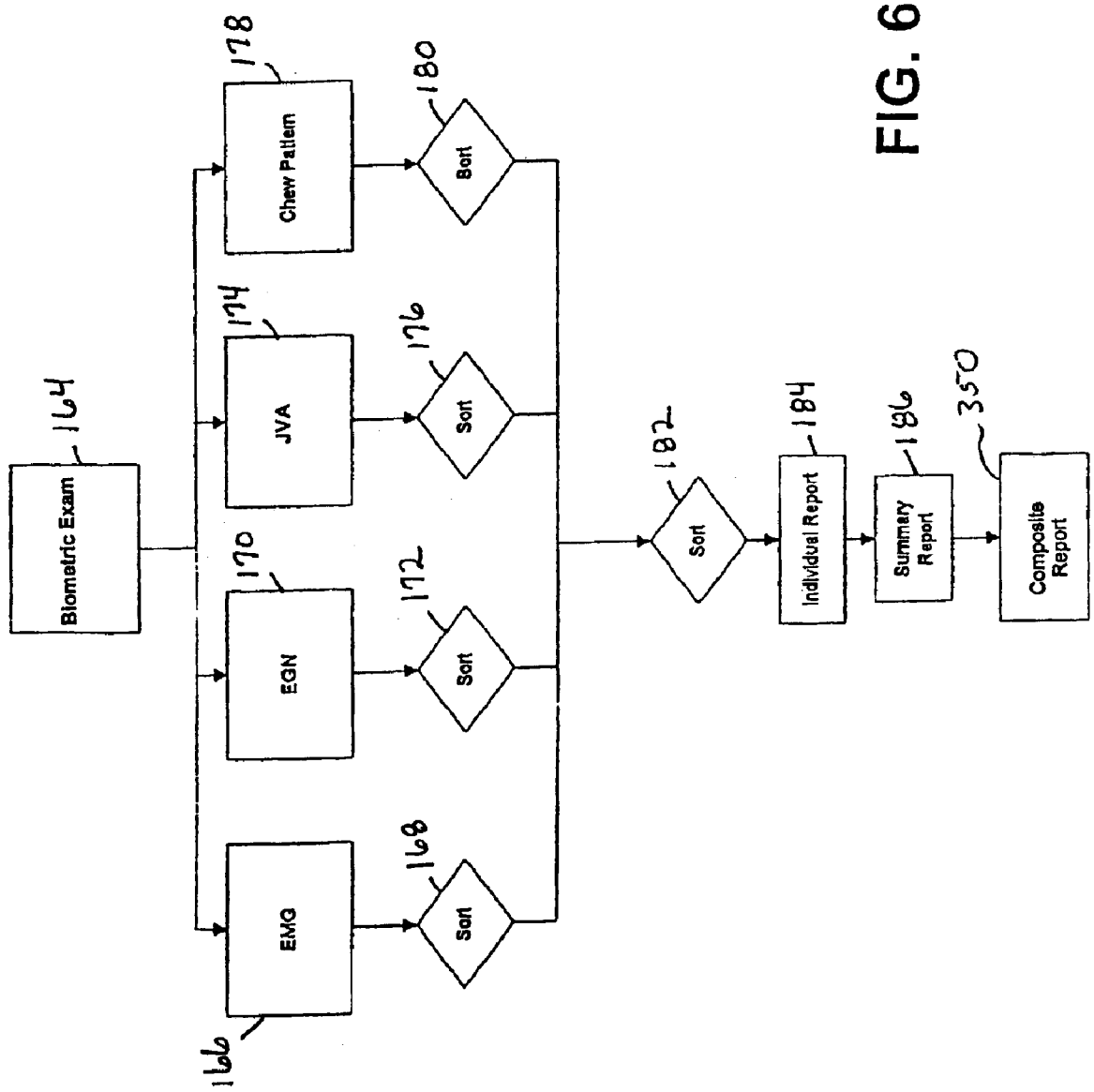
FIG. 6 is a diagrammatic flow chart of a biometric examination module.

The next step in this system is the biometric muscular exam module 164, as shown in FIG. 6. This module allows healthcare workers to measure the bioactivity of several key muscle groups related to the oral apparatus. The first measurement is the electromyographic measurement for muscular activity at 166. This allows the healthcare professional to record the electromyographic measurement (EMG) of key oral muscles by using the measured activity between the left and right side muscles. Data as a result of the EMG test is then sorted at 168.

The second text conducted is the electrognathography (EGN) test at 170. The EGN is a magnetic recording of mandible movement, both vertically and laterally. It records the smoothness and speed of jaw movement, while simultaneously recording any right or left deviation. Data from this exam is then sorted at 172.

The next biometric exam recorded is the temporomandibular joint vibration analysis (JVA) at 174. This exam measures joint activity. Specifically, as the condyle moves along the glanoid fossa in function, the condylar disc responds and moves with the condylar. Typically, very little noise is produced. If there is, however, any pathologic changes, such as arthritic changes, or the disc is damaged, noise characteristics of the condylar disc will be changed and the distinct vibration can be recorded. Analysis of the different vibration sound waves from the condylar disc can indicate damage to same. Data from this exam is sorted at 176. Finally, the chew pattern can be taken at 178, with data sorted at 180. The chew pattern measures the occlusal forces exerted on the teeth when the same are brought together. Once all the data has been collected and sorted as described above, they can then be sorted together at 182, and individual and summary reports 184 and 186, respectively, can be generated, as well as contribute to the composite report 350.

Figure 7:
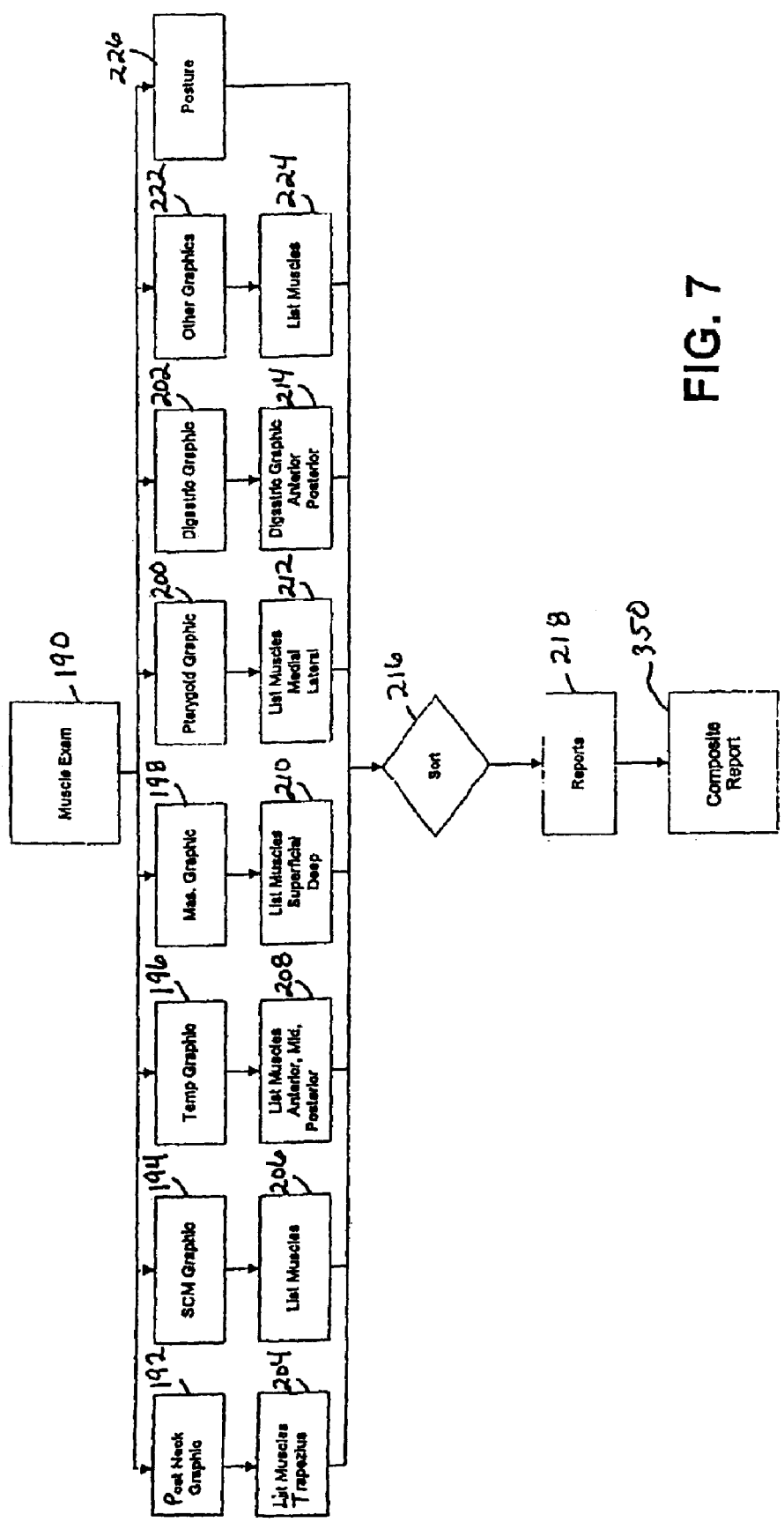
FIG. 7 is a diagrammatic flow chart of a muscular examination module.

An examination of specific muscle groups 190 is shown in FIG. 7. Module 190 allows a physician to examine and record the data of specific muscle groups believed to have an impact on TMJ. Data from the following muscle groups are recorded for further analysis, including the posterior neck muscle group at 192. This muscle group is responsible for head posture and movement. A sternocleidomastoid muscle group is examined at 194. This group is responsible for lateral head movement. The temporal muscle group exam is conducted at 196. This muscle group is responsible for mandible movement. The masseter muscle group is analyzed at 198, and this group is responsible for lower jaw movement during chewing when teeth are in contact. Next, the pterygoid muscle group is examined at 200. This group is responsible for jaw movement back and forth, sideways, and opening of the mouth. Finally, the digastric muscle group is examined at 202. This group is responsible for lowering the mandible and elevating the hyoid bone. In each case with the muscle exams 192 through 202, the relevant muscles are listed at 204 through 214, respectively, and sorted at 216 for generating report 218 and contribute to the composite report 350. Additionally, the physician can examine other muscle groups at 222, listing those muscles at 224, if it is believed, based on complaints from the patient, that other muscle groups may be involved other than those listed in 204 through 214. And because posture can always play a role and affect such muscles, section 226 allows the physician to further evaluate the patient's body posture, and record any notable facets of it.

Figure 8:
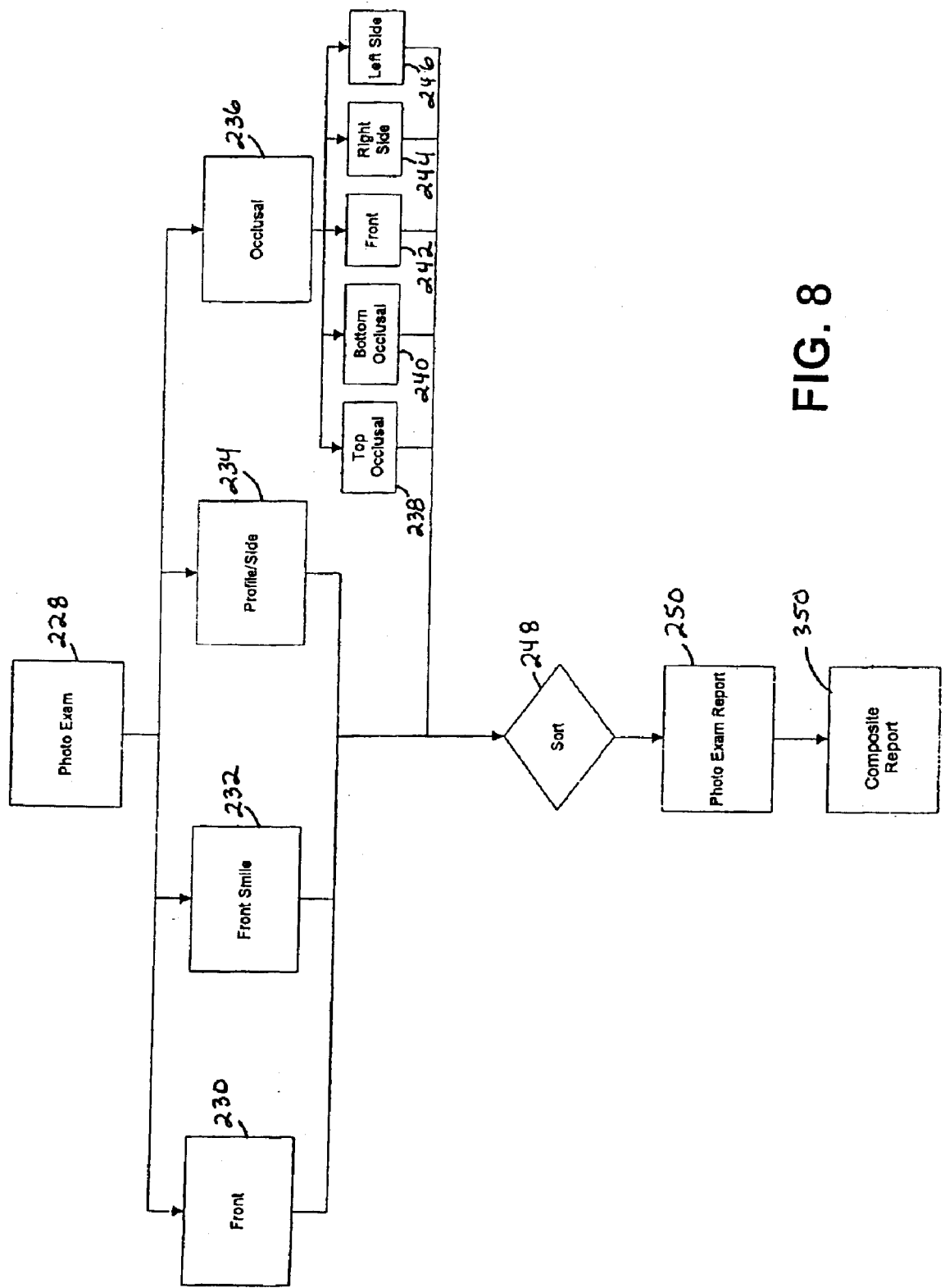
FIG. 8 is a diagrammatic flow chart of a photo examination module.

A photo exam module 228 is shown in FIG. 8. Such photos include a front photo 230, a front smile photo at 232, and a profile side photo at 234. In addition, a battery of occlusal photos are taken at 236. The battery of occlusal photos include top at 238, bottom at 240, front at 242, and right and left side at 244 and 246, respectively. It is contemplated that module 228 then sorts the photos at 248, and photo exam report is issued at 250 which contributes to composite report 350.

Figure 9:
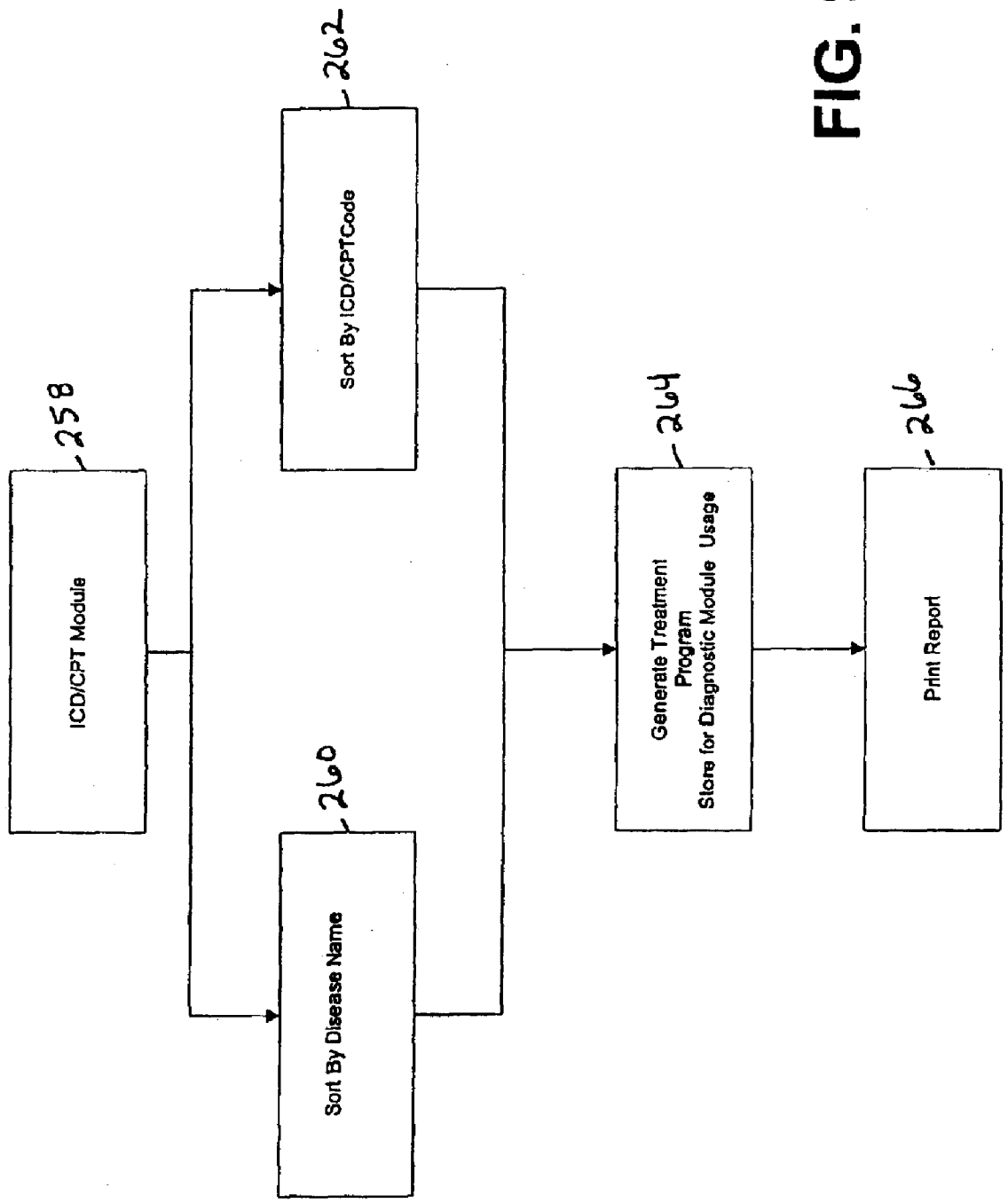
FIG. 9 is a diagrammatic flow chart of a ICD/CPT module.

The ICD/CPT module 258, as shown in FIG. 9 illustratively lists each disease's signs and symptoms, with the recommended treatment protocol. It is contemplated that as the treatment protocol is expanded, or the disease's signs and symptoms are further qualified, the user can easily update this information into the database, allowing for clarification of diagnosis and treatment. It is further contemplated that data from the various exams and symptoms can be entered by its respective ICD code, CPT code. In the illustrated embodiment, the physician may use module 258 to research various diseases or treatment protocols by searching by disease name at 260 or its ICD or CPT code at 262. Resulting reports can be generated and printed at 264 and 266, respectively. The physician may then use that information in conjunction with the diagnostic module 300 to develop treatment protocols for a particular diagnosis such as TMJ. Specifically, the treatment protocols are stored in the system at 264 for use with diagnostic module 300, as shown in FIG. 1.

Figure 10:
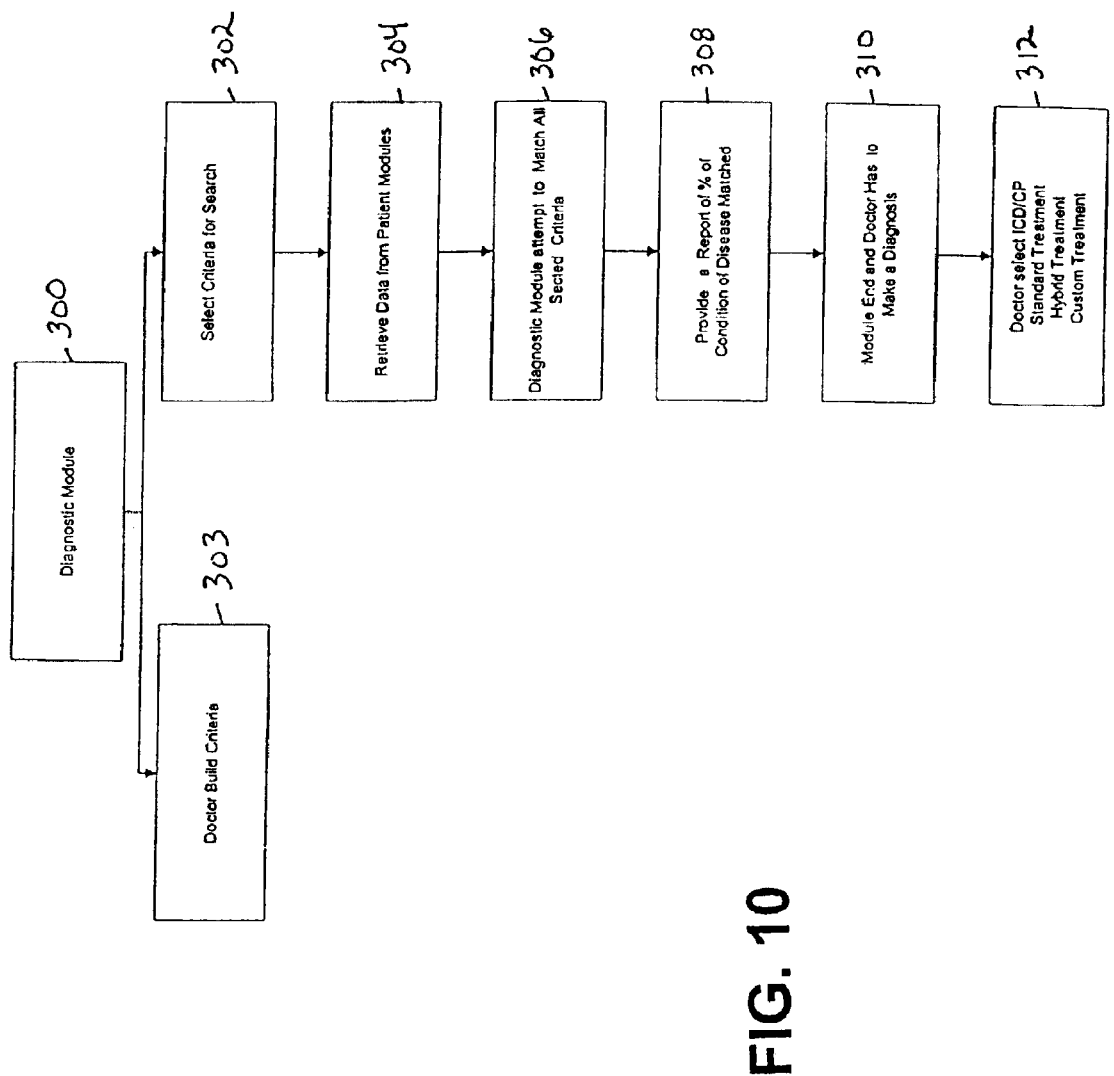
FIG. 10 is a diagrammatic flow chart of a diagnostic condition criteria module.

As shown in FIGS. 1 and 10, the overall system 1 is structured in such a way that all patient personal, medical, dental, and diagnostic data is warehoused in the system. In the diagnostic module 300 the known disease diagnostic criteria is also warehoused and is communicable with the data from the other modules 2, 28, 62, 92, 169, 190. In the illustrative embodiment, diagnostic module 300 allows the doctor to select a condition with a set of diagnostic criteria from the database at 302 or build his or her own criteria at 303. In the case of selecting criteria from the database 302, the conditions may be based on location of body, symptoms, signs, medical tests, mitigating factors and aggravating factors. Matches 304 are then retrieved from the other modules 2, 28, 62, 92, 169, 190. It is contemplated that the module 300 will find patients with either complete matches 306 of the diagnostic criteria, or a partial match 308 of the diagnostic criteria. For those patients with a complete match of the diagnostic criteria, the doctor can then chose an appropriate treatment protocol. The doctor can choose the treatment protocol 310 derived from the ICD/CPT module 258, a custom treatment protocol developed by the physician, or a hybrid of the ICD and custom treatment protocols at 312.

In another illustrative embodiment, module 300, or even a separate module can be included that communicates with other like modules from other physicians through a network or other similar system, so that diagnosis, diagnostic criteria and treatment protocols can be shared. This allows the physician to evaluate a much broader range of diagnosis and treatment options for his or her patients.

Although the present disclosure has been described with reference to particular means, methods and embodiments, from the foregoing description, one skilled in the art can easily ascertain the essential characteristics of the invention and various changes and modifications may be made to adapt the various uses and characteristics without departing from the spirit and scope of the invention as set forth in the following claims.

What is claimed is:

1. A method of assisting in diagnosing and treating temporomandibular joint disease of a patient comprising:

providing a database configured to receive and sort data;

conducting an examination of the patient, said examination comprising a plurality of medical tests related to temporomandibular joint disease;

inputting results of the examination into the database;

determining the symptoms experienced by the patient;

inputting the symptoms being experienced by the patient into the database;

matching the results of the examination and the symptoms in the database with known diagnostic criteria for temporomandibular joint disease; and receiving a treatment protocol from the database based on the matching of the results and symptoms with the known diagnostic criteria.

2. The method of claim 1, further comprising the step of inputting a treatment protocol and results of said treatment protocol.

3. The method of claim 2, wherein the database comprises case successful treatment protocols of temporomandibular joint disease.

4. The method of claim 1, further comprising the step of inputting patient and insurance information for payment and treatment authorization.

5. The method of claim 1, further comprising the step of inputting case histories from a plurality of patients.

6. The method of claim 5, wherein the case histories comprise symptoms related to temporomandibular joint disease.

7. A system for assisting diagnosis and treatment of temporomandibular joint disease comprising:
- a computer system in communication with a database that is configured to receive data of modules containing data, as well as output data;
- a symptoms module that records and stores a plurality of symptom data related to temporomandibular joint disease experienced by a plurality of patients;
- a medical examinations module that comprises data from a plurality of medical examinations related to temporomandibular joint disease on each of the plurality of patients;
- a diagnostic module in communication with the symptoms and medical examinations modules;
- wherein the diagnostic module comprises a plurality of diagnostic criteria based on conditions known to be a factor in diagnosis of temporomandibular joint disease such that an operator can create a selected diagnostic criteria to establish a basis for diagnosis of temporomandibular joint disease; and
- wherein the diagnostic module searches the plurality of symptom data and the data from the plurality of medical examinations and compares the data with the selected diagnostic criteria to find a match to the selected diagnostic criteria; and
- a treatment module in communication with the diagnostic module;
- wherein a treatment protocol is selected based on the match between the symptoms and examinations data and the selected diagnostic criteria.

8. The system of claim 7, wherein the diagnostic criteria is selected from at least one of a group consisting of locations of pain, symptoms, medical examinations, and mitigating and aggravating circumstances.

9. The system of claim 7, wherein the medical examinations are selected from at least one of a group consisting of a dental exam, an x-ray exam, a biometric exam and a muscle exam.

10. The system of claim 7, wherein the match of the selected diagnostic criteria is a complete match or a partial match.

* * * * *